(12) United States Patent
Maeda et al.

(10) Patent No.: US 9,724,476 B2
(45) Date of Patent: Aug. 8, 2017

(54) MEDICAL RUBBER PARTS

(71) Applicant: SUMITOMO RUBBER INDUSTRIES, LTD., Kobe-shi, Hyogo (JP)

(72) Inventors: Katsushi Maeda, Kobe (JP); Yoshikazu Masuyama, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 309 days.

(21) Appl. No.: 14/469,656

(22) Filed: Aug. 27, 2014

(65) Prior Publication Data

US 2015/0086802 A1   Mar. 26, 2015

(30) Foreign Application Priority Data

Sep. 25, 2013 (JP) ................. 2013-198587

(51) Int. Cl.
| | | |
|---|---|---|
| *A61M 5/315* | (2006.01) | |
| *A61J 1/06* | (2006.01) | |
| *A61J 1/14* | (2006.01) | |
| *B29C 43/20* | (2006.01) | |
| *B29C 43/14* | (2006.01) | |
| *B65D 39/00* | (2006.01) | |
| *B29L 9/00* | (2006.01) | |
| *B29L 31/26* | (2006.01) | |
| *B29L 31/00* | (2006.01) | |
| *B29K 23/00* | (2006.01) | |
| *B29K 105/24* | (2006.01) | |
| *B29K 105/00* | (2006.01) | |

(52) U.S. Cl.
CPC .......... *A61M 5/31513* (2013.01); *A61J 1/065* (2013.01); *A61J 1/1412* (2013.01); *B29C 43/145* (2013.01); *B29C 43/203* (2013.01); *B65D 39/0052* (2013.01); *A61M 2205/02* (2013.01); *A61M 2207/00* (2013.01); *B29K 2023/22* (2013.01); *B29K 2105/0032* (2013.01); *B29K 2105/246* (2013.01); *B29K 2995/0056* (2013.01); *B29L 2009/00* (2013.01); *B29L 2031/265* (2013.01); *B29L 2031/7544* (2013.01); *Y10T 428/31924* (2015.04)

(58) Field of Classification Search
CPC .......... A61M 5/31513; A61M 2205/02; A61M 2207/00; A61J 1/065; A61J 1/1412; B29C 43/145; B29C 43/203; B65D 39/0052; Y10T 428/31924; B29K 2023/22; B29K 2105/0032; B29K 2105/246; B29K 2995/0056; B29L 2009/00; B29L 2031/265; B29L 2031/7544
See application file for complete search history.

(56) References Cited

U.S. PATENT DOCUMENTS

| | | | |
|---|---|---|---|
| 4,366,912 A | 1/1983 | Matukura et al. | |
| 2016/0075485 A1* | 3/2016 | Masuyama et al. | .. B29C 43/021 215/364 |

FOREIGN PATENT DOCUMENTS

| | | | |
|---|---|---|---|
| EP | 1020277 A1 | 7/2000 | |
| GB | 2256615 A | 12/1992 | |
| JP | 58-39436 A | 3/1983 | |
| JP | 63-43104 B2 | 8/1988 | |
| JP | 7-41065 B2 | 5/1995 | |
| JP | 2816905 B2 | 10/1998 | |
| JP | 10-314305 A | 12/1998 | |
| JP | 2000-334025 | * 12/2000 | ................ A61J 1/05 |

OTHER PUBLICATIONS

Extended European Search Report, dated Feb. 19, 2016, for European Application No. 15177526.9.

* cited by examiner

*Primary Examiner* — Nathan M Nutter

(74) *Attorney, Agent, or Firm* — Birch, Stewart, Kolasch & Birch, LLP

(57) ABSTRACT

The present invention provides, medical rubber parts that do not physically and chemically affect the quality of preparations. The present invention relates to a medical rubber part obtained by press-molding an unvulcanized rubber mainly containing a rubber for forming a liquid-contacting portion and an unvulcanized rubber mainly containing a butyl-based rubber for forming a non-liquid-contacting portion, wherein a color difference dE between the liquid-contacting portion and the non-liquid-contacting portion is 6.0 or more in NBS units.

6 Claims, 3 Drawing Sheets

(a)

(b)

MEDICAL RUBBER PARTS

TECHNICAL FIELD

The present invention relates to medical rubber parts such as a vial rubber stopper, a pre-filled syringe gasket, and a nozzle cap.

BACKGROUND ART

Rubber parts for medical use are known to have possible physical and chemical effects on the quality of preparations depending on the kind of preparation. For example, nitrile butadiene rubber (NBR) and hydrogenated nitrile butadiene rubber (HNBR) are excellent in oil resistance; however, since they are synthesized by emulsion polymerization, an emulsifier, coagulant or other components added in polymerization may be extracted in drugs, particularly causing adverse effects on the drugs. On the other hand, fluorinated rubber, silicone rubber, fluorinated silicone rubber, acrylonitrile butadiene rubber, hydrogenated acrylonitrile butadiene rubber, epichlorohydrin rubber, and butyl-based rubber are excellent in terms of the quality stability of preparations but poor in needle penetration and airtightness.

In this context, a medical rubber stopper is known which includes fluororubber on the liquid-contacting side and butyl rubber laminated to the fluororubber. Such a rubber stopper, however, has the problem of poor productivity because it is prepared by applying an adhesive to a raw material stopper formed of fluororubber, and loading the stopper into a mold for final, molding to laminate the stopper to butyl rubber. Also, a rubber stopper whose liquid-contacting portion is laminated with a fluororesin film has been developed. Such a stopper is prepared by a two-step molding process in which a raw material stopper leg portion (liquid-contacting portion) is first formed and then a final product is formed. Thus, the molding step and the punching step each need to be carried out twice, which disadvantageously creates a complication resulting in poor productivity (Patent Literature 1).

CITATION LIST

Patent Literature

Patent Literature 1: JP-A H10-314305

SUMMARY OF INVENTION

Technical Problem

The present invention aims to provide medical rubber parts that do not physically and chemically affect the quality of preparations.

Solution to Problem

Thus, the present invention is directed to press molding using an unvulcanized rubber mainly containing a rubber that does not adversely affect drugs, for forming a liquid-contacting portion, and an unvulcanized rubber mainly containing a butyl-based rubber for forming a non-liquid-contacting portion, and aims to achieve both the reduction of adverse effects on drugs and simplification of production. The present invention further has the feature that the color difference dE between the liquid-contacting portion and the non-liquid-contacting portion is increased so that when formed in press molding, defective products in which the butyl-based rubber for forming the non-liquid-contacting portion is undesirably moved to the liquid-contacting portion side can be visually screened out.

Specifically, the present invention relates to a medical rubber part, obtained by press-molding an unvulcanized rubber mainly containing a rubber for forming a liquid-contacting portion and an unvulcanized rubber mainly containing a butyl-based rubber for forming a non-liquid-contacting portion, wherein a color difference di between the liquid-contacting portion and the non-liquid-contacting portion is 6.0 or more in NBS units.

The color difference di is preferably 12.0 or more in NBS units.

Preferably, in the unvulcanized rubber for forming a liquid-contacting portion or a non-liquid-contacting portion, an amount of color pigments other than titanium oxide is 0 to 3.0 parts by mass and an amount of titanium oxide is 0 to 5.0 parts by mass, each per 100 parts by mass of a rubber component of the unvulcanized rubber.

A density difference between the liquid-contacting portion and the non-liquid-contacting portion is preferably 0.02 or less.

The present invention also relates to a vial rubber stopper, a pre-filled syringe gasket, and a nozzle cap each including the medical rubber part.

Advantageous Effects of Invention

The medical rubber parts of the present invention are obtained by press molding using an unvulcanized rubber mainly containing a rubber that does not adversely affect drugs, for forming a liquid-contacting portion, and an unvulcanized rubber mainly containing a butyl-based rubber for forming a non-liquid-contacting portion. Thus, they can achieve both the reduction of adverse effects on drugs and simplification of production. Further, the medical rubber parts have a large color difference dE between the liquid-contacting portion and the non-liquid-contacting portion, which makes it possible to easily visually screen out defective products in which a part formed of the butyl-based rubber for forming the non-liquid-contacting portion is undesirably moved to the liquid-contacting portion side.

DESCRIPTION OF EMBODIMENTS

The medical rubber parts of the present invention are medical rubber parts obtained by press-molding an unvulcanized rubber mainly containing a rubber for forming a liquid-contacting portion and an unvulcanized rubber mainly containing a butyl-based rubber for forming a non-liquid-contacting portion, wherein the color difference dE between the liquid-contacting portion and the non-liquid-contacting portion is 6.0 or more in NBS units.

The rubber for forming a liquid-contacting portion is preferably a rubber that can maintain the quality stability of drugs. Examples thereof include brominated isobutylene p-methylstyrene copolymer rubber, fluororubber, fluorosilicone rubber, acrylonitrile butadiene copolymer rubber, hydrogenated acrylonitrile butadiene copolymer rubber, and ethylene propylene copolymer rubber. Some of these rubbers are poor in some properties such as extractables levels, needle penetration, and airtightness. However, by laminating them to a butyl-based rubber, both preparation stability and rubber stopper properties can be achieved.

For example, fluororubber is superior to other synthetic rubbers in terms of chemical resistance, oil resistance, and low adsorption of preparations, but is poor in needle penetration. This problem can be solved by using fluororubber on the liquid-contacting side and laminating it to butyl rubber.

Acrylonitrile butadiene-based rubber (NBR, HNBR) is excellent in oil resistance and thus is particularly used for oily preparations. However, it shows higher extractables levels than other polymers in the test for rubber closure for aqueous infusions in conformity with the Japanese Pharmacopoeia, Sixteenth Edition (hereinafter abbreviated as "JP16"). This is caused by residues of the emulsifier, coagulant, and other components added in the polymerization of NBR or HNBR. To solve this problem, acrylonitrile butadiene-based rubber can be used on the liquid-contacting side and laminated to butyl rubber to provide a rubber stopper which is excellent in oil resistance and meets the requirements of the test for rubber closure for aqueous infusions.

Ethylene propylene copolymer rubber (EPR) can be used with high-pH preparations but is poor in resilience when it is pierced by a needle. This problem can be solved by using ethylene propylene copolymer rubber on the liquid-contacting side and laminating it to butyl rubber.

Examples of the butyl-based rubber for forming a non-liquid-contacting portion include butyl rubber and halogenated butyl rubber. Butyl rubber is excellent in gas impermeability. In particular, halogenated butyl rubber is excellent in heat resistance and extractables levels.

Figure 1:
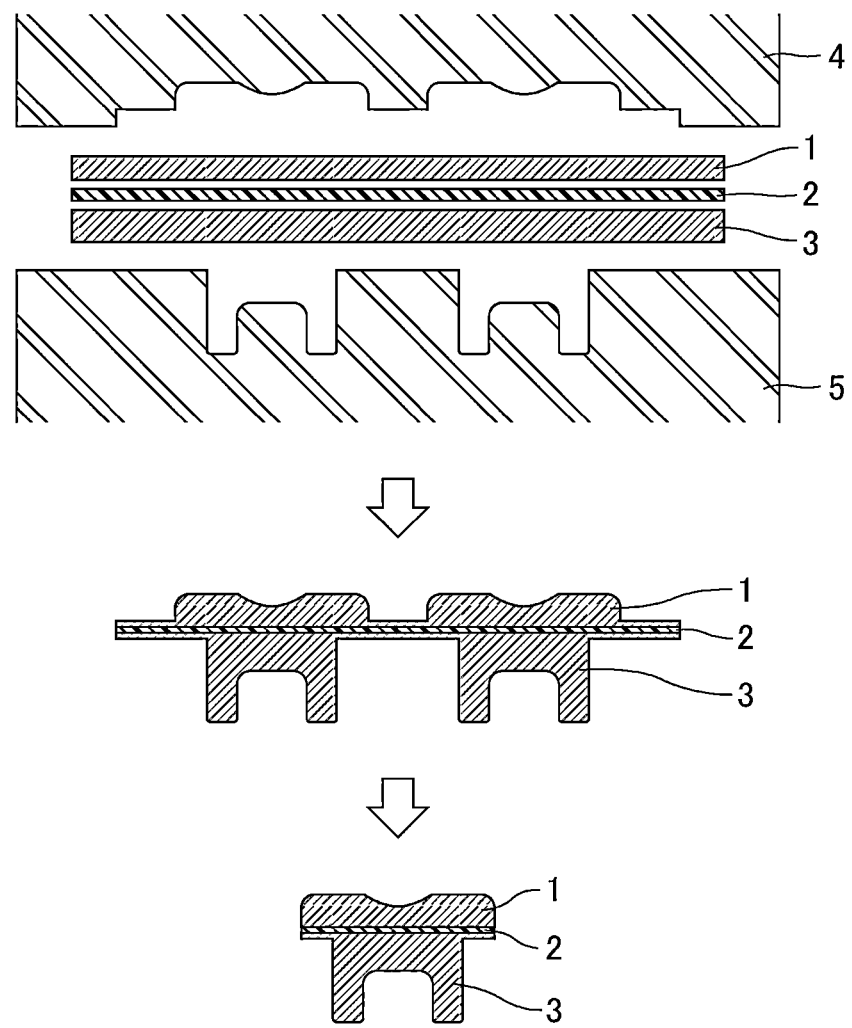
FIG. 1 is an explanatory view for showing a method for the production of a medical rubber part of the present invention.

The medical rubber parts of the present invention can be obtained by press molding using an unvulcanized rubber mainly containing a rubber for forming a liquid-contacting portion and an unvulcanized rubber mainly containing a butyl-based rubber for forming a non-liquid-contacting portion. The press molding is a method of molding an unvulcanized rubber by pressing the rubber in a mold to form a shape, and examples thereof include single-step and two-step molding processes. Single-step molding is preferred for its simplification. The single-step molding herein refers to a process in which an article is formed and punched out into a final shape in one molding operation as shown in FIG. 1. In the method, for example, an unvulcanized rubber sheet or rubber ribbon is positioned between an upper mold 4 and a lower mold 5, heated and compressed under vacuum by a compression or vacuum press or the like to form a molded sheet including a set of products of a certain shape, which are then punched out into a final product shape. Alternatively, injection molding may be employed in which an unvulcanized rubber is pressure-injected from an injection gate and molded. The single-step molding process is different from the two-step molding process in which a liquid-contacting' portion (a raw material stopper leg portion) is first prepared and then a final product is formed, in other words, the molding step and the punching step are each performed twice. Consequently, the production process by single-step molding is greatly simplified compared to by two-step molding.

In a rubber stopper produced by two-step molding, since only a part or the bottom of the lea portion is laminated with a resin film or covered with a rubber for preparation stability, the rubber may be swelled in a drug permeating from the leg portion. In the case that a rubber stopper is produced by single-step molding, the liquid-contacting portion is covered with a rubber that is excellent in the quality stability of drugs. Thus, permeation of drugs can be suppressed to prevent swelling of the rubber in the non-liquid-contacting portion; moreover, extraction from the non-liquid-contacting portion can be suppressed to prevent a reduction in the quality of drugs. For example, in a medical rubber stopper thus produced, the lower face (liquid-contacting portion) of a top-face flange portion is entirely covered with a rubber that is excellent in the quality stability of drugs. Thus, such a medical rubber stopper can suppress permeation of drugs to prevent swelling of the rubber in the top-face flange portion corresponding to a non-liquid-contacting portion, and can also suppress extraction from the non-liquid-contacting portion to prevent a reduction in the quality of drugs.

An unvulcanized rubber sheet is prepared by kneading rubbers that can be used as the rubber component with a kneader, roll mill, or the like. An unvulcanized rubber sheet for forming a liquid-contacting portion and an vulcanized rubber sheet for forming a non-liquid-contacting portion may be stacked by any method. In one method, for example, unvulcanized rubbers are separately formed, weighed and cut into sheets by a calender roll or sheet preforming machine, and then stacked just before molding. In another method, unvulcanized rubbers are simultaneously passed through a calender roll to be bonded and cut.

In order to bond an unvulcanized rubber sheet for forming a liquid-contacting portion and an unvulcanized rubber sheet for forming a non-liquid-contacting portion, an adhesive film (e.g. an ultra high molecular weight polyethylene film) may be laminated therebetween. In the present invention, which utilizes a butyl-based rubber as the unvulcanized rubber for forming a non-liquid-contacting portion, when the rubber component of the unvulcanized rubber sheet for forming a liquid-contacting portion includes a rubber other than brominated isobutylene p-methylstyrene copolymer rubber, acrylonitrile butadiene copolymer rubber, and hydrogenated acrylonitrile butadiene copolymer rubber (e.g. fluororubber, fluorosilicone rubber, ethylene propylene copolymer rubber), an adhesive film can be preferably used to greatly improve the adhesion between the rubber sheets.

Figure 2:
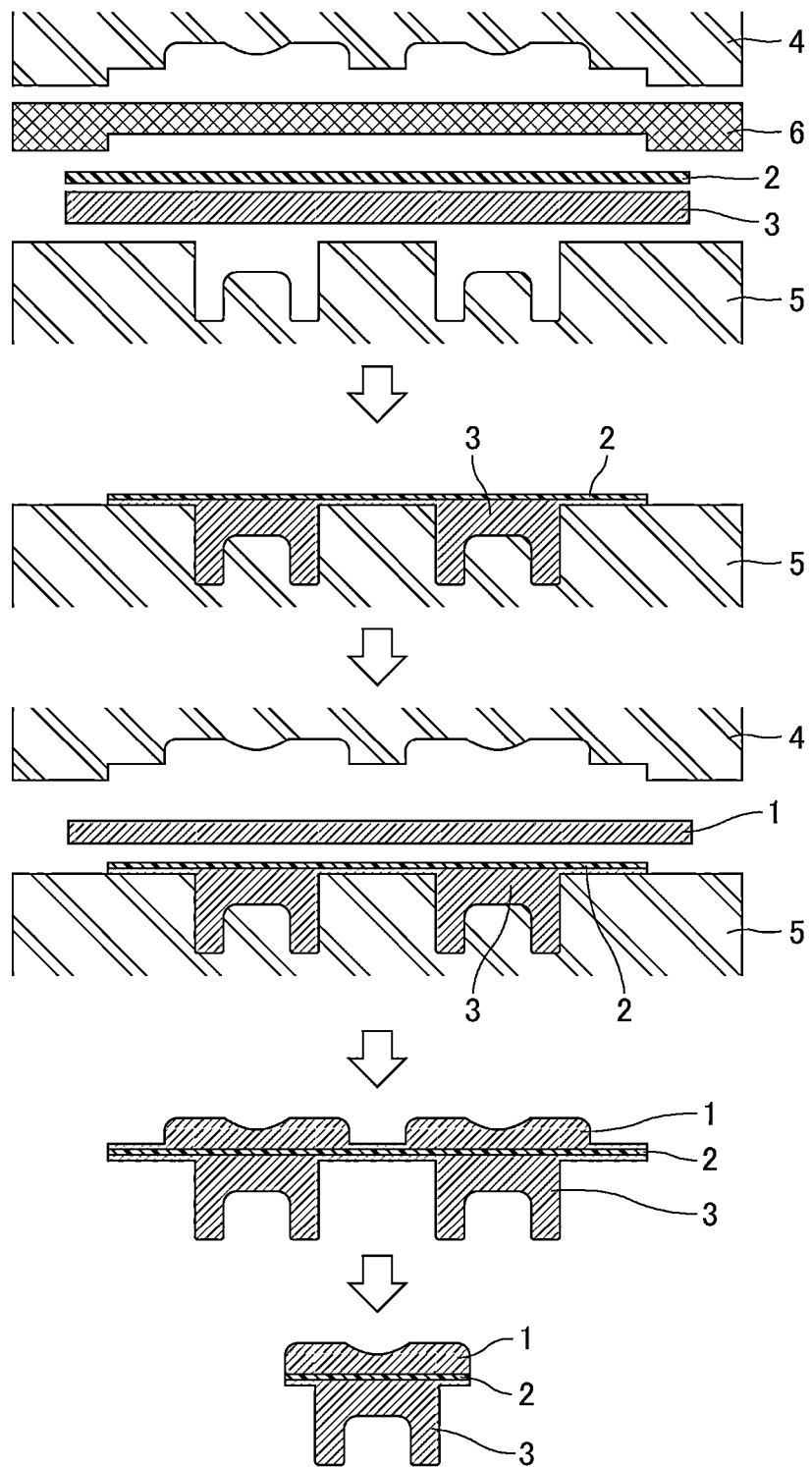
FIG. 2 is an explanatory view for showing another method for the production of a medical rubber part of the present invention.

FIG. 2 shows another embodiment of the single-step molding process. In this embodiment, an adhesive film 2 is laminated to an unvulcanized rubber sheet 3 for forming a liquid-contacting portion, and the stack is heated and compressed under vacuum between a middle mold 6 and a lower mold 5 to form a molded sheet including a set of products of a certain shape. Then, an unvulcanized rubber sheet 1 for forming a non-liquid-contacting portion is superimposed on the molded sheet without punching out. The resulting stack is heated and compressed under vacuum by a compression or vacuum press or the like between an upper mold 4 and the lower mold 5 to form a molded sheet including a set of products of a certain shape, which are then punched out to provide a final product part.

The color difference dE between the liquid-contacting portion and the non-liquid-contacting portion is 6.0 or more, preferably 12.0 or more, in NBS units. The National Bureau of Standards established rating criteria to describe color differences by NBS units. A color difference of not less than 6.0 NBS units is rated as "very significant color difference" and a color difference of not less than 12.0 NBS units is rated as "showing different colors". With such a color difference, a defective molded product in which the butyl-based rubber is undesirably moved to the liquid-contacting side, when formed in molding, can be easily found by visual inspection and excluded. Thus, the time for individual inspection is shortened so that the work efficiency of inspectors can be improved.

In the press molding, two unvulcanized rubber sheets are stacked and pressed with heat. Here, the rubber materials flow in complex patterns in the mold. Since pressure varies depending on the position of the cavity of the mold, the rubber materials do not flow in a fixed pattern in the mold. For example, in a rubber stopper for use in freeze drying, since the shape of a part of the leg portion forming the liquid-contacting portion is varied to form a horseshoe (single-legged) or two-legged shape or the like, the rubber materials flow in complex patterns according to the shape of the rubber stopper. Thus, the butyl-based rubber used for forming the non-liquid-contacting portion (on the top-face flange side) may appear in the liquid-contacting portion due to molding pressure, resulting in a defective product. In another case, the rubber for forming the liquid-contacting portion, conversely, may appear in the non-liquid-contacting portion (on the flange side). Such a phenomenon tends to be significant especially when single-step molding is performed. The present invention is suitable for rubber parts having such complicated shapes, especially produced by single-step molding.

To adjust the color difference dE between the liquid-contacting portion and the non-liquid-contacting portion to 6.0 or more, color pigments such as inorganic pigments and organic pigments may be added to the rubber materials. Examples of the inorganic pigments include titanium oxide (rutile type with strong hiding and coloring powers and anatase type), carbon black (e.g. channel black, furnace black, thermal black, acetylene black), red iron oxide, and barite. Examples of the organic pigments include azo pigments and lake pigments. These color pigments are desirably used in the form of a masterbatch for the purpose of avoiding color tone variations among production lots. The color pigments may be added to either the liquid-contacting portion or the non-liquid-contacting portion, or both.

The amount of titanium oxide as a white pigment, among these color pigments, is preferably 0 to 5.0 parts by mass and more preferably 0 to 3.0 parts by mass per 100 parts by mass of the rubber component. Also, the amount of color pigment (a) other than titanium oxide is preferably 0 to 3.0 parts by mass and more preferably 0 to 2.0 parts by mass per 100 parts by mass of the rubber component. When color pigment (s) other than titanium oxide is used, the lower limit of its amount is 0.01 parts by mass. When titanium oxide is only used, the lower limit of its amount is 0.5 parts by mass.

In addition to the color pigments, compounding agents such as filler (e magnesium oxide, silica, talc, clay), polyethylene, a crosslinking activator, a silane coupling agent, a softener, and a fatty acid may be added.

The density difference between the liquid-contacting portion and the non-liquid-contacting portion is preferably 0.02 or less and more preferably 0.01 or less. The control of the number of medical rubber parts is important to control packing quantity, shipping quantity, and stocks. Although the method for counting the number of rubber parts varies depending on product mass, the mass of 10 to 100 rubber parts is measured and converted to the mass corresponding to a desired packing quantity before rubber parts are counted and packed. In the case of rubber parts having no laminated structure, variations in product mass can generally be caused by variations in density from kneading lot to kneading lot and in the burr thickness of each molded sheet. Hence, these items are controlled to control the number of products. In a case where rubber materials greatly differing in specific gravity are laminated by single-step molding, product mass can vary depending on the thickness of each unvulcanized rubber sheet, the difference in pressing pressure according to the position of the mold, and the like. By adjusting the density difference between the rubber for forming the liquid-contacting portion and the butyl-based rubber for forming the non-liquid-contacting portion to 0.02 or less, the number of laminated rubber parts can be controlled in the same manner as for non-laminated rubber parts.

The density of a rubber part is determined depending on the kinds of raw material rubber, filler, reinforcing agent, processing aid and other additives and their amounts. Regarding raw material rubbers, for example, butyl-based rubber has a density of 0.92 to 0.93, whereas fluororubber (1.86) fluorosilicone rubber (1.42), and epichlorohydrin rubber (1.27) each have a higher density. Accordingly, the density difference between the butyl-based rubber in the top-face flange portion and each of the latter rubbers tends to be difficult to set to ±0.02. In the case of brominated isobutylene p-methylstyrene copolymer rubber (0.93), IR (0.91), BR (0.90), EPDH (0.87), NBR (0.98) and the like, the density difference can be easily adjusted to 0.02 or less by controlling the amount of additives such as filler and reinforcing agent.

The present invention also relates to a vial rubber stopper, a pre-filled syringe gasket, and a nozzle cap each including the medical rubber part described above. The above-described medical rubber parts of the present invention do not physically and chemically affect the quality of preparations, and therefore is suitable as medical rubber parts such as vial rubber stoppers, pre-filled syringe gaskets, and nozzle caps.

The medical rubber parts of, the present invention are produced by the above-described single-step molding. In the case of applying a silicone lubricant, the silicone lubricating coating agent is applied to a sheet-shaped molded product including a large number of continuous rubber stoppers. Moreover, the medical rubber parts are produced by the steps of: inspecting the appearance of each sheet before punching out rubber parts; punching out an individual rubber stopper; performing cleaning, sterilization and drying; inspecting the appearance; and packing.

Figure 3:
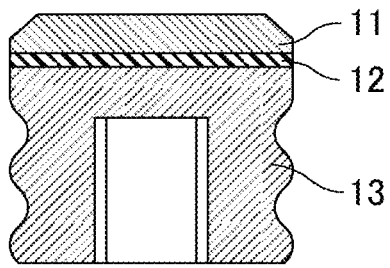
FIG. 3 is a cross-sectional view of a pre-filled syringe gasket of the present invention.

FIG. 3 is a cross-sectional view of a pre-filled syringe gasket of the present invention. The portion indicated by 11 is the liquid-contacting portion, the portion indicated by 13 is the non-liquid-contacting portion, and the portion indicated by 12 is a cut portion punched out in single-step molding.

EXAMPLES

The present invention is more specifically described by reference to examples but is not limited only to these examples.

Hereafter, chemicals used in preparation examples are listed.
Chrolinated butyl rubber: HT1066 (JSR Corporation)
Polyethylene (LDPE): FLO-THENE UF (Sumitomo Seika Chemicals Co., Ltd.)
Magnesium oxide: KYOWA NAG 150 (Kyowa Chemical Industry Co Ltd.)

Synthetic silica: Nipsil LP (TOSOH SILICA CORPORATION)
Fine talc: Mistron CB (Luzenac America, Inc.)
Calcined clay: Satintone H (ENGELHARD CORPORATION)
Titanium oxide: TIPAQUE A100 (ISHIHARA SANGYO KAISHA, LTD.)
Thermal black: Thermax MT (Cancarb)
Crosslinking agent: 6-R-1,3,5-triazine-2,4-dithiol (SANKYO KASEI Co., Ltd.)
HNBR: DN2020L (ZEON CORPORATION)
NBR: Perbunan 3346F (LANXESS)
Crosslinking activator: TMPT (SHIN-NAKAMURA CHEMICAL CO., LTD.)
Crosslinking agent: PERHEXA 25B-40 (NOF CORPORATION)

Examples 1 and 2, and Comparative Example 1

An ultra high molecular weight polyethylene film (thickness: 100 μm) was sandwiched between an unvulcanized butyl rubber sheet (thickness: 1.21 mm) for forming a non-liquid-contacting portion and a nitrile rubber sheet (thickness: 1.5 mm) for forming a liquid-contacting portion in accordance with the formulations in Table 1. The stack was subjected to single-step molding with a vacuum press at 170° C. for 10 minutes to prepare a 5-ml vial rubber stopper.

<Density>
The specific gravity of each unvulcanized rubber sheet was measured using an automatic densimeter (hydrostatic densimeter) (TOYO SEIKI SEISAKU-SHO, LTD.).

<Color Difference>
The color difference in NBS units between unvulcanized rubber sheets was measured three times using a colorimeter (CR-221, KONICA MINOLTA), and the average of the measured values was determined as the color difference between these rubber sheets.

<Adhesion Strength>
The adhesion strength was measured at 50 mm/min in conformity with JIS K6256-1.

<Extractables Testing>
The extractables testing was performed on each medical rubber part in conformity with JP16 "test for rubber closure for aqueous infusions". The test items and specification values are mentioned below.
Description: clear and colorless
Transparency: 99.0% or more at both wavelengths of 430 cm and 650 nm
UV absorption spectrum: absorbance of 0.2 or less at a wavelength of 220 to 350 mm
Foam test: disappeared within three minutes
pH: within ±1.0
Zinc: 1 μg/mL or less
$KMnO_4$-reducing substances: 2.0 mL/100 mL or less
Residue on evaporation: 2 mg or less <Individual Inspection>
Defective molded products in which the butyl rubber to be on the non-liquid-contacting portion appeared in (or entered) the liquid-contacting portion were marked in the molded sheet of each example. The sheets were then subjected to punching out, cleaning, and drying, followed by picking up the marked defective products. Next, 10 defective molded products were mixed with good products to give a total of 500 products in each example. The mixed products were visually inspected by three persons to determine the detection rate.

Figure 4:
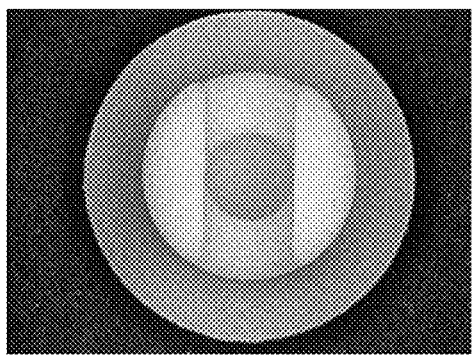
FIG. 4 represents photographs showing the appearance of a medical rubber part of the present invention and a defective medical rubber part.
Figure 4:
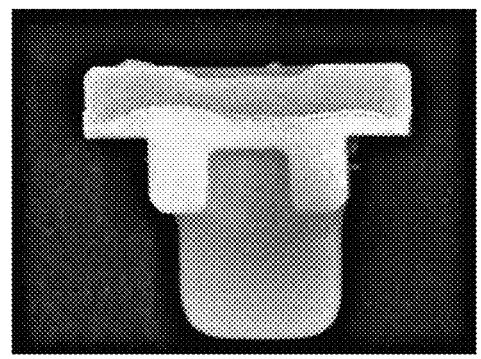
Figure 4:
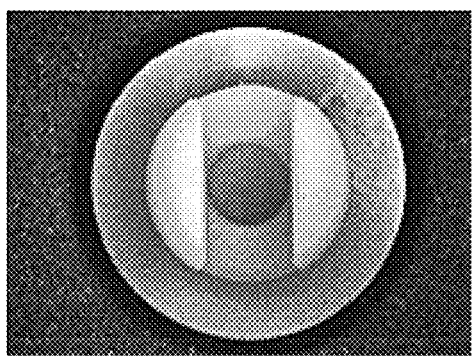
Figure 4:
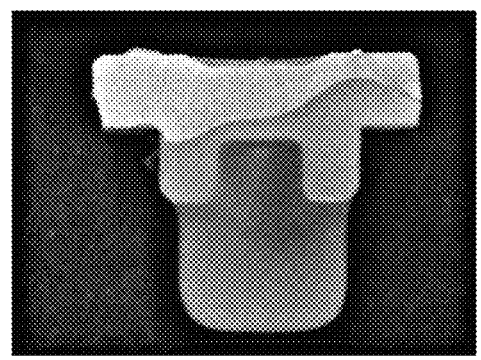

FIG. 4 shows bottom views (left side) and cross-sectional views (right side) of the vial rubber stoppers thus produced. The views of the good product are indicated by (a), and the views of the defective product are indicated by (b). In the good product, the rubber for forming the non-liquid-contacting portion was not undesirably moved to the lower flange face in the liquid-contacting portion. In contrast, in the defective product, a part of the rubber material for forming the non-liquid-contacting portion was undesirably moved to the lower flange face, in other words, the rubber for the non-liquid-contacting portion also formed the liquid-contacting portion. Thus, it is highly possible that such a rubber stopper physically and chemically affects the quality of preparations.

TABLE 1

| | Example No. | | Example 1 | Example 2 | Comparative Example 1 | Comparative Example 2 |
|---|---|---|---|---|---|---|
| Non-liquid-contacting portion | HT1066 | | 100 | 100 | 100 | — |
| | Polyethylene (LDPE) | | 5 | 5 | 5 | — |
| | Magnesium oxide | | 3 | 3 | 3 | — |
| | Synthetic silica | | 10 | 10 | 10 | — |
| | Fine talc | | 25 | 25 | 25 | — |
| | Calcined clay | | 10 | 10 | 10 | — |
| | Coloring pigments: | Titanium oxide | 3 | 3 | 3 | — |
| | | Thermal black | 0.25 | 0.25 | 0.25 | — |
| | Crosslinking agent (triazine) | | 1.5 | 1.5 | 1.5 | — |
| | Molding conditions | | 170° C., 10 min. | 170° C., 10 min. | 170° C., 10 min. | — |
| | Density (g/cm$^3$) | | 1.160 | 1.160 | 1.160 | — |
| Liquid-contacting portion | HNBR DN2020L | | 30 | 30 | 30 | 30 |
| | NBR (medium-high AN type) | | 70 | 70 | 70 | 70 |
| | Polyethylene (LDPE) | | 2 | 2 | 2 | 2 |
| | Magnesium oxide | | 2 | 2 | 2 | 2 |
| | Talc | | 20 | 20 | 20 | 20 |
| | Calcined clay | | 10 | 10 | 10 | 10 |
| | Coloring pigments: | Titanium oxide | 1.5 | — | 1.5 | 1.5 |
| | | Thermal black | 0.15 | — | 0.2 | 0.2 |
| | Crosslinking activator TMPT | | 2 | 2 | 2 | 2 |
| | Crosslinking agent PERHEXA 25B-40 | | 1 | 1 | 1 | 1 |
| | Conditions in single-step molding | | 170° C., 10 min. | 170° C., 10 min. | 170° C., 10 min. | 170° C., 10 min. |
| | Density (g/cm$^3$) | | 1.155 | 1.147 | 1.155 | 1.155 |

TABLE 2

| | | Example 1 | | | Example 2 | | | Comparative Example 1 | | | Comparative Example 2 |
|---|---|---|---|---|---|---|---|---|---|---|---|
| Color difference between liquid-contacting portion and non-liquid-contacting portion | NBS (dE) | 7.1 | | | 20.7 | | | 3.9 | | | — |
| Density difference between liquid-contacting portion and non-liquid-contacting portion | (g/cm$^3$) | 0.005 | | | 0.013 | | | 0.005 | | | — |
| Adhesion strength | (N/cm) | 21.8 | | | 22.7 | | | 20.9 | | | — |
| | Judgement | Good | | | Good | | | Good | | | |
| Defect rate in inspection of molded sheet | (%) | 1.1 | | | 1.5 | | | 1.1 | | | — |
| Indivisual inspection | Detected number (pcs) | 10 | 10 | 10 | 10 | 10 | 10 | 8 | 8 | 7 | — — — |
| | Detection rate (%) | 100 | 100 | 100 | 100 | 100 | 100 | 80 | 80 | 70 | |
| JP16 Extractables testing | | Appropriate | | | Appropriate | | | Appropriate | | | Inappropriate pH, KMnO$_4$-reducing substances |

In Example 1, the color difference dE was 6.0 or more which is regarded as "very significant color difference". In Example 2, the color difference dE was 12.0 or more which is regarded as "showing different colors". Therefore, the defective molded products were easily found by visual inspection, resulting in high inspection accuracy.

Comparative Example 2

In accordance with the formulation in Table 1, an unvulcanized rubber sheet was prepared. The unvulcanized rubber sheet (2.5-mm thick) was molded by a vacuum press at 170° C. for 10 minutes to prepare a 5-ml vial rubber stopper. Since such a rubber stopper does not have a two-layer structure, defective products as found in two-layer rubber stoppers are not formed.

However, this rubber stopper, which was formed of a single rubber layer, was poor in pH stability and inappropriate in terms of KMnO$_4$-reducing substances in the JP16 extractables testing.

REFERENCE SIGNS LIST 1 unvulcanized rubber sheet for forming a non-liquid-contacting portion
2 adhesive film
3 unvulcanized rubber sheet for forming a liquid-contacting portion
4 upper mold
5 lower mold
6 middle mold
11 liquid-contacting portion
12 cut (punched out) portion
13 non-liquid-contacting portion

The invention claimed is:

1. A medical rubber part, obtained by:
stacking an unvulcanized rubber sheet mainly containing a rubber for forming a liquid-contacting portion and an unvulcanized rubber sheet mainly containing a butyl-based rubber for forming a non-liquid-contacting portion, and
press-molding the stacked rubber sheets to form a molded sheet, thereby obtaining said medical rubber part,
wherein a color difference dE between the liquid-contacting portion and the non-liquid-contacting portion is 6.0 or more in NBS units, and
wherein a density difference between the liquid-contacting portion and the non-liquid-contacting portion is 0.02 or less.

2. The medical rubber part according to claim 1, wherein the color difference dE is 12.0 or more in NBS units.

3. The medical rubber part according to claim 1, wherein in the unvulcanized rubber for forming a liquid-contacting portion or a non-liquid-contacting portion, an amount of color pigments other than titanium oxide is 0 to 3.0 parts by mass and an amount of titanium oxide is 0 to 5.0 parts by mass, each per 100 parts by mass of a rubber component of the unvulcanized rubber.

4. A vial rubber stopper, comprising the medical rubber part according to claim 1.

5. A pre-filled syringe gasket, comprising the medical rubber part according to claim 1.

6. A nozzle cap, comprising the medical rubber part according to claim 1.

* * * * *